United States Patent [19]

Saudagar

[11] Patent Number: 4,670,313
[45] Date of Patent: Jun. 2, 1987

[54] METHOD FOR PARTING RUBBER AND PRODUCTS FORMED THEREBY, AND A METHOD OF MAKING A BLOOD VESSEL

[75] Inventor: Abdul S. Saudagar, Irvine, Calif.

[73] Assignee: Polymed Laboratories, Tustin, Calif.

[21] Appl. No.: 844,522

[22] Filed: Mar. 27, 1986

Related U.S. Application Data

[63] Continuation of Ser. No. 665,295, Oct. 26, 1984.

[51] Int. Cl.⁴ ............... A45B 19/00; A61M 31/00
[52] U.S. Cl. ............................. 428/12; 428/36; 604/53; 604/93; 604/96
[58] Field of Search ........... 604/96, 53, 93; 428/36, 428/12; 427/2, 393.5, 407.1

[56] References Cited

U.S. PATENT DOCUMENTS

| | | | |
|---|---|---|---|
| 2,132,501 | 10/1938 | Watkins | 106/38.22 |
| 3,424,607 | 1/1969 | Coscia | 427/133 |
| 3,460,975 | 8/1969 | Stebleton | 427/2 |
| 3,585,647 | 6/1971 | Gajewski et al. | 427/2 X |
| 4,055,682 | 10/1977 | Merrill | 427/2 |
| 4,266,999 | 5/1981 | Baier | 427/2 X |
| 4,292,965 | 10/1981 | Nash et al. | 427/2 X |
| 4,331,736 | 5/1982 | Schäfer et al. | 427/393.5 X |
| 4,548,844 | 10/1985 | Podell et al. | 427/322 X |

Primary Examiner—Thurman K. Page
Attorney, Agent, or Firm—Spensley Horn Jubas & Lubitz

[57] ABSTRACT

Disclosed are several methods of parting rubber from an underlying surface. Polyvinyl alcohol, methylcellulose, starch derivatives and dextran are all suitable parting agents for rubber. Polyvinyl pyrrolidine is a particularly effective parting agent for use in the formation of balloon-type medical catheters; it is also useful as a parting agent in the formation of synthetic membranes, blood vessels and conduits. The invention includes the method of use of these parting agents as well as the products formed by the disclosed process(es). Also disclosed is a method of forming a synthetic blood vessel of a polymer material, e.g., polyurethane.

9 Claims, 7 Drawing Figures

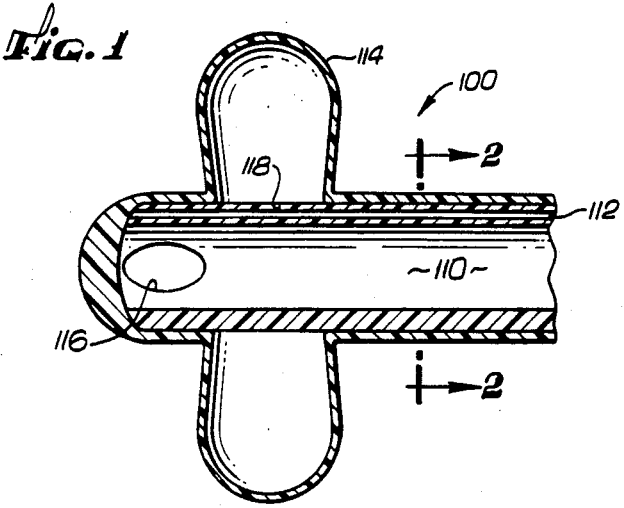
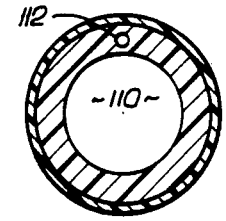
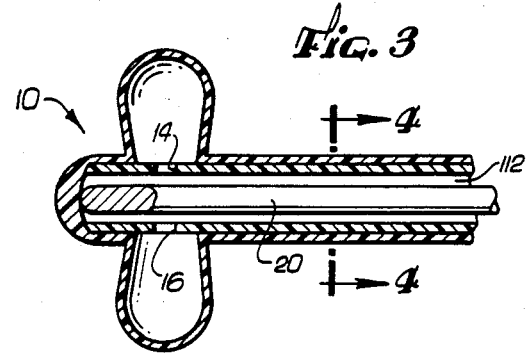
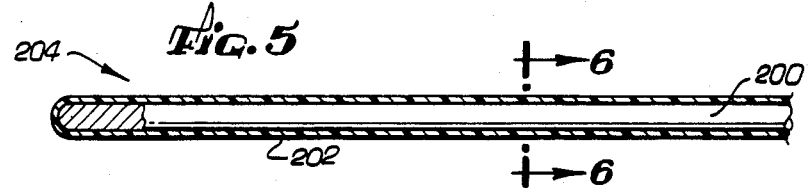
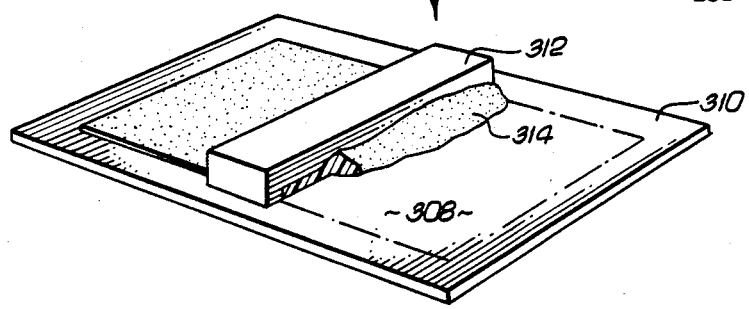

METHOD FOR PARTING RUBBER AND PRODUCTS FORMED THEREBY, AND A METHOD OF MAKING A BLOOD VESSEL

This is a continuation of U.S. patent application Ser. No. 665,295 filed on Oct. 26, 1984.

BACKGROUND OF THE INVENTION

1. Field of the Invention

The invention relates to:

(1) a method of parting rubber from a surface and certain products formed from this process; and (2) a method of making a synthetic blood vessel using a parting agent.

2. The Problems Associated with Known Balloon Catheters and Their Production Methods Balloon-type catheters have numerous medical applications. They can be used for drainage (e.g. urethral, Foley, colostomy, ileostomy and septostomy catheters), as diagnostic aids (e.g. thermodilution catheters), for therapeutic purposes (e.g. embelectomy, tansluminal agioplasty, endotracheal, tracheostomy, esophageal, and intra-aortic catheters), and in a wide variety of other medical applications.

To date, many of the known methods of making balloon catheters have had serious deficiencies. For example, most methods were complex, required repeated attempts to achieve successful practice, and, as a consequence, were costly. Additionally, and more importantly, virtually all the known processes produce a seriously deficient product. For example, the methods disclosed in U.S. Pat. Nos. 3,292,627, 3,304,353 and 3,452,756 all produce a catheter with a thermoplastic and/or polyurethane balloon layer. Thermosplastic balloons, following inflation, do not revert to their original shape and size. Furthermore, polyurethane balloons are unsuitable for certain in vivo uses as urine hydrolyzes polyurethane.

U.S. Pat. No. 3,983,879 discloses a method for making a silicone rubber balloon-type catheter. In this patent it is stated that silicone is more compatible with body tissues than the thermoplastic materials of the '627, '353 and '756 patents. In the '879 patent process, tape is first wrapped around the inflation hole, the inflation hole being the hole which leads to the catheter's inflation lumen. The tape serves to prevent adherence of the balloon layer to the catheter tubing when the tubing is dipped in a solution of the material which forms the balloon layer. Following the formation of the balloon layer, the hole is re-opened with a hot probe.

This process, in addition to being complex, costly, requiring precision labor, and being subject to error—particularly at the stage where the probe is used to re-open the inflation hole—produces a deficient product because:

(a) the tape forms annular shoulders at the respective ends of the wrappings; this can cause patient irritation as well as difficult catheter withdrawal and insertion during in vivo catheter use;

(b) re-opening of the hole with the hot probe can result in a weak spot in the balloon layer as the probe must be passed through the balloon layer;

(c) the tape is wrapped around the tubing in an overlapping fashion thereby forming an irregular surface and resulting in an irregular balloon layer;

(d) it is difficult to re-open the hole as it is hidden from view by the tape wrapping;

(e) melting the tape can result in fragmentation of the tape—should the balloon break during in vivo catheter use, tape fragments can enter the body;

(f) tape fragmentation could also cause tape fragments to enter the balloon inflation hole thereby preventing in vivo balloon deflation and making catheter withdrawal difficult.

Thus, what is needed is a process for making balloon catheters which is easy to practice, inexpensive, and produces a balloon catheter without the deficiencies of the known products. The catheter should be made of a bio-compatible material which is not hydrolyzed by body fluids. The balloon layer should be made of a material which reverts to its original shape following inflation; there should be no ostensible ridges or surface irregularities in the balloon layer vicinity. Furthermore, there should be no ostensible weak spots in the balloon layer and no non-compatible materials within the balloon layer.

SUMMARY OF THE INVENTION

In one aspect, the invention includes the method of use of certain parting agents for rubber, (e.g. silicone rubber), as well as the resulting products. Such parting agents include polyvinyl pyrrolidine (PVP), a water soluble grade of polyvinyl alcohol, methylcellulose, starch derivatives and dextran. These parting agents are all water soluble and allow easy and complete separation of a rubber skin from an underlying surface. In addition, certain of these parting agents have special applicability as they are bio-compatible and non-thrombogenic.

In practicing the invention, a solution of rubber is applied over a parting agent. After forming an elastomer skin, the skin is separated from the surface underlying the parting agent. A variety of products, for example, catheters, conduits, and synthetic membranes and blood vessels can be formed using this process. Due to its bio-compatible nature, silicone rubber is a preferred rubber.

In a preferred embodiment, the parting agent used is in solution. However, it is also possible to apply the parting agent in a solid form.

Polyvinyl pyrrolidine is a preferred parting agent because it is bio-compatible. When PVP, or other of the above-mentioned parting agents, is dried and cured, it becomes brittle thereby making its structure easy to disrupt. Following disruption, the silicone rubber skin is readily separable from the underlying surface even without the addition of water or other solvent(s).

The invention further includes, in a preferred embodiment, the use of polyvinyl pyrrolidine as a parting agent in the making of balloon-type medical catheters, as well as the catheters themselves. In a typical procedure, a PVP coating is applied to the surface of silicone rubber tubing in an area near one or more lumen hole(s). The coating is dried and cured, (e.g. at a temperature of about 150° F.), a solution of silicone rubber is applied over the PVP coating, and, following curing of the silicone rubber thereby forming a silicone rubber elastomer skin, the PVP coating can be mechanically disrupted. As the PVP coating is brittle from the elevated temperature curing, mechanical disruption usually fully separates the skin from the tubing and also opens the inflation hole. The product is now ready for use.

It is also possible to delete this disrupting step because the parting agent coating will become so brittle after curing that by merely inflating the balloon with gas or liquid, the balloon will be fully released.

The advantages of this process over the known processes include:

(a) it is easy and inexpensive to practice—the use of silicone rubber solution allows bonding of the skin to the tubing without any extra attachment steps;

(b) the inflation hole is easily opened.

The advantages of the product formed by this process include:

(1) the catheter and the PVP are comparatively low allergenic and bio-compatible thereby lessening potential danger and discomfort;

(2) there are no surface irregularities or shoulders formed in the area of the balloon layer, thus, in vivo insertion and withdrawal of the catheter is essentially atraumatic;

(3) the catheter has a long shelf life;

(4) the catheter can be sterilized by virtually any known method;

(5) the catheter can be re-used upon resterilization;

(6) the catheter is not hydrolyzed by body fluids, e.g., urine;

(7) the catheter's physical and chemical properties do not change at or near body temperature;

(8) the balloon layer reverts to its original shape and size even after repeated inflation and deflation;

(9) there are no ostensible weak spots in the balloon layer;

(10) a relatively thin-walled extruded catheter tubing with a correspondingly large drainage lumen and drainage capacity can be used to form drainage catheters, e.g., Foley catheters;

(11) as silicone rubber attracts less salt deposits than do conventional plastics, it thereby aids in preventing formation of intra-bladder stones and is thus well-suited for use in urinary drainage catheters;

(12) a urinary drainage catheter can be made having a short distance from the balloon to the end of the catheter—this catheter design allows near complete bladder drainage and minimal bladder irritation upon drainage;

(13) the rubber balloon layer can be made so that upon inflation, a donut-shaped balloon rather than a conventional rounded-shaped balloon is formed—this donut-shape aids in preventing inadvertent catheter removal and also provides a larger intracorporeal contact surface area, and thus less patient discomfort, than encountered with a conventional, rounded balloon;

(14) the balloon can generally be fully released simply by manually disrupting the PVP coating or by inflating with water or air.

While a preferred embodiment PVP is used as the parting agent for forming balloon catheters, it is also possible to use other parting agents, e.g., dextran, a water soluble grade of polyvinyl alcohol, methylycellulose, or starch derivatives.

In another aspect, the invention includes the making of catheters, conduits, and synthetic membranes and blood vessels of rubber or silicone rubber, using any of the above-mentioned parting agents.

The invention further comprises the making of synthetic blood vessels using a suitable polymer, e.g., polyurethane, and any of the above-mentioned parting agents.

BRIEF DESCRIPTION OF THE DRAWINGS

FIG. 1 is a side sectional view of one end of urinary drainage catheter with the balloon portion fully inflated.

FIG. 2 is a sectional view of the catheter of FIG. 1 taken along the line 2—2.

FIG. 3 is a side sectional view of one end of an embolectomy catheter with the balloon portion fully inflated.

FIG. 4 is a sectional view of the catheter of FIG. 3 taken along the line 4—4.

FIG. 5 illustrates a cylindrical mandrel upon which a synthetic vascular graft (shown in sectional perspective) can be cast.

FIG. 6 is a sectional view of the mandrel of FIG. 5 taken along with the line 6—6.

FIG. 7 depicts an apparatus suitable for the formation of a synthetic membrane.

DETAILED DESCRIPTION OF THE INVENTION

Example 1: Formation of a Silicon Rubber Embolectomy Catheter

The catheter tubing used in forming an embolectomy catheter is an extruded section of medical grade silicone purchased from Dow-Corning, with an outer diameter of approximately 0.1" and an inner diameter approximately $\frac{1}{3}$ the outer diameter. Two inflation holes are drilled opposite each other approximately one to one and one-half inch from one end of the tubing. Following drilling, the catheter tubing is thoroughly cleaned in reagent grade ethyl alcohol in order to remove any particulate matter and/or debris resulting from the drilling of the inflation holes.

To impart the necessary rigidity to the catheter a stainless steel wire mandrel, having a diameter slightly less than that of the tubing inner diameter, is inserted into the tubing.

A ring of polyvinyl pyrrolidine is applied to the outer surface of the tubing in the area of the inflation holes. This can be performed, for example, by rotating the catheter and brushing on a solution of approximately 10% w/w, 360,000 molecular weight polyvinyl pyrrolidine (purchased from Polysciences, Inc.), in reagent grade ethyl alcohol. The catheter rotation can be performed by clamping both ends of the tubing with pin holders which are in turn attached to a band marking fixture, the fixture being driven by a motor and gear system. A slight tension in the tubing may be maintained to avoid sag in the tubing.

Other methods of applying the PVP coating are also of course possible. Furthermore, PVP with a molecular weight of less than 360,000 may be used, however solution viscosity will be lower for a given PVP concentration. Consequently, if using lower molecular weight PVP, one must increase the solution concentration to make it suitable for paintbrush application as the solution must not be so thin that it drips into the inflation holes and thereby enters the tubing. One should rather form a bridge of PVP over the hole.

Following coating, the coated tubing is dried and cured in an oven at approximately 150° F. for 15-30 minutes or longer. Thereafter, the end portions of the tubing which have been in contact with the pin holders are cut off. By way of this cutting procedure, the distance from the inflation hole(s) to the end of the tubing can be adjusted as desired.

The balloon layer is deposited by dipping the coated end of the tubing in a solution of medical grade silicone dissolved in a suitable solvent, for example, xylene, toluene, or 1,1,1-trichloroethane. These silicone solutions are sold under the tradenames: Silastic 07-2213 Medical Grade Silicone Dispersion (Dow-Corning) and, 521001 Medical Grade Silicone Elastomer (International Silicone Corporation). Solvents of other elastomeric solutions which do not dissolve the parting agent coating are also within the scope of the invention.

The balloon layer deposit step can be repeated as desired until a satisfactory balloon wall thickness is achieved. However, the rubber deposit should be dried after the application of each successive layer.

Upon achieving the desired balloon thickness, the catheter is dried for about one hour at about 150° F. and then cured at about 200°-250° F. for 30-60 minutes. Curing the balloon portion at such elevated temperatures results in a brittle PVP coating which can then be mechanically disrupted by simply squeezing the balloon portion. This squeezing will usually completely release the balloon from the tubing. The balloon can now be inflated with either liquid or gaseous means.

It should be noted that silicone solutions are available which can be cured at room temperature thereby making the elevated temperature curing step(s) unnecessary. Although with use of such silicone solutions, the coating will not become brittle, use of these solutions is within the scope of the invention. Furthermore, while silicone is a preferred rubber for use in most medical applications due to its inert properties, use of other rubbers is also within the scope of the invention.

FIGS. 3 and 4 depict an embelectomy catheter 10 formed by the above-described process. Catheter 10 has two inflation holes 14 and 16, and a central bore 12. Running through bore 12 is a wire mandrel 20. The two inflation holes are provided so that the balloon will evenly inflate on either side of the catheter. However, having only one hole, or having more than two holes, is also within the scope of the invention. Furthermore, catheters having more than one balloon are also within the scope of the invention.

Example 2: Formation of a Urinary Drainage Catheter

By a procedure analogous to that described in Example 1, but instead using a tubing with a central bore 110 and an inflation lumen 112, (such as the tubing 102 shown in FIGS. 1 and 2), a urinary drainage catheter can be made. The complete procedure will be readily apparent to those skilled in the art.

FIG. 1 shows a urinary drainage catheter 100 with a balloon 114, a drainage hole 116, and an inflation hole 118. Drainage hole 116 must be re-opened following formation of the catheter 100. The balloon 114 is shown in the fully inflated position in FIG. 1, and it can be seen that the balloon 114 assumes a donut shape when fully inflated.

Example 3: Formation of Other Balloon-Type Catheters

By a process analogous to that described in Examples 1 and 2, as will be apparent skilled in the art, one can make the following balloon-type catheters: cardiovascular diagnostic, cardiovascular therapeutic, and cardiovascular monitoring balloon catheters (e.g. thermodilution and transluminal angioplasty catheters); endotracheal and tracheostomy tubes; self-retaining urinary, colostomy, and ileostomy balloon-type conduits and drainage tubes; septostomy balloon catheters, (e.g. Rashkind septostomy catheter); intra-aortic balloon catheters; esophageal balloon catheters.

It is possible to use any of the other parting agents, e.g., polyvinyl alcohol, methylcellulose, starch derivatives, or dextran with the procedures described in any of the above examples. The precise method of use of these parting agents is well known by those skilled in the art.

It should be understood that the parting agents and balloon materials used with any of the abovementioned catheters should be bio-compatible. Balloons often rupture during in vivo use and the body interior is thereby exposed to any parting agent which is beneath the balloon layer. PVP is a particularly preferred parting agent as it is very bio-compatible. Silicone rubber is a preferred rubber for making the balloon as if it ruptures, it tends to tear or puncture rather than shattering into multiple fragments as do certain other rubbers. Such fragments can cause a variety of problems, for example, thrombogenesis if the fragments enter the bloodstream.

Additionally, silicone is a preferred material for forming the catheter tubing. With catheters made of certain plastics or other materials, it is necessary to apply a heparin coating thereto to prevent thrombogenesis. Silicone is relatively non-thrombogenic; thus, heparin coating is unnecessary. Moreover, silicone rubber possesses anti-adhering properties. Thus, neither the balloon layer nor the PVP will tend to adhere to the tubing and balloon release is therefore facilitated.

Example 4: Formation of a Synthetic Blood Vessel

Referring to FIGS. 5 and 6, glass, stainless steel or teflon mandrel 200 is first dipped in a solution of parting agent 202, which is for example, PVP or a water soluble grade of polyvinyl alcohol. The coating is dried in an oven for 15 to 30 minutes at 150° F. The coated mandrel 204 is then dipped into a solution of silicone or polyurethane or any other blood compatible polymer. This dipping is repeated until the desired wall thickness of the blood vessel is obtained. However, the deposits should be dried after the application of each successive layer. Due to the properties of the parting agent, e.g., easy disruption, the vascular graft can be easily removed from the mandrel, for example, by soaking in water to thereby dissolve the parting agent. A preferred polymer for forming the synthetic blood vessel is polyurethane.

Example 5: Formation of a Synthetic Ureter

By a process essentially identical to that described in Example 4, but using silicone rubber as the preferred polymer, a synthetic ureter can be formed. As mentioned previously, urine hydrolyzes polyurethane and not silicone rubber.

Example 6: Formation of a Synthetic Membrane

Using a membrane formation block, such as block 300 depicted in FIG. 7, one can form a synthetic membrane as follows.

A suitable parting agent for this procedure includes any of PVP, water soluble grades of PVA, starch derivatives, methylcellulose or dextran. The parting agent 308 is first applied to the surface 310 (which is, for example, a glass, metal or Teflon (TM) plate) and silicone rubber 314 in solution is then applied over the parting agent with a film-casting block 312 which has a substantially U-shape. Following drying and curing of the silicone rubber, it can be removed from the surface 310 (e.g., with water) thus leaving a layer of silicone rubber which is suitable for use as an artificial membrane. Polyvinyl pyrrolidine, as it is bio-compatible, is a particularly well-suited parting agent.

Other modifications and variations of the invention will be apparent to those skilled in the art; the terms and expressions used herein are terms of description only and not of limitation, the scope of the invention being only limited by correct interpretation of the claims which follow.

As used in the claims, the term "rubber" includes natural and synthetic rubbers.

What is claimed is:

1. The product formed by making a synthetic membrane through the steps of:
   (a) coating a catheter surface having a lumen hole with a parting agent so as to form a band about the catheter at the postion of the lumen hole;
   (b) applying a skin of polymeric material over the parting agent coating;
   (c) drying and/or curing the skin and separating it from the catheter surface; and
   (d) removing any residue of said parting agent coating existing between said separated skin and said catheter surface; said product CHARACTERIZED IN THAT:
   after separation of the skin from the catheter surface, forming proximate to the lumen hole in said catheter surface a balloon layer, said balloon layer being physically contiguous with said catheter surface and without external irregularities or shoulders formed at a periphery of said balloon layer; and further
   wherein said balloon layer will form upon inflation through said lumen hole a donut-shaped balloon circumferentially about the catheter surface.

2. The product formed by the steps of:
   (a) coating a catheter surface, having a lumen hole, so as to form a band on the catheter at the position of the lumen hole with a parting agent which is in solution and is one of polyvinyl pyrrolidine, a water soluble grade of polyvinyl alcohol, methylcellulose, starch derivatives, or dextran;
   (b) applying a skin of polymeric material which is silicone rubber in solution;
   (c) drying and/or curing the skin and separating it from the surface;
   (d) removing any residue of said parting agent coating existing between said separated skin and said surface; wherein drying the parting agent coating is accomplished prior to application of the polymeric material; and
   wherein curing said polymeric material is accomplished after its application; said product CHARACTERIZED IN THAT:
   after separation of the skin from the catheter surface, forming proximate to the lumen hole in said surface a balloon layer, said balloon layer being physically contiguous with said catheter surface and without external irregularities or shoulders formed at a periphery of said balloon layer; and further
   wherein said balloon layer will form upon inflation through said lumen hole a donut-shaped balloon circumferentially about the catheter surface.

3. The product formed by the process of:
   (a) coating a catheter surface having a lumen hole with a parting agent in a band circumferentially around the catheter at the position of the lumen hole;
   (b) applying a skin of polymeric material over the parting agent coating;
   (c) drying and/or curing the skin; and
   (d) separatihg said skin by contacting said catheter surface with water thereby dissolving and removing the parting agent coating and allowing release of the skin; said product CHARACTERIZED IN THAT:
   after separation of the skin from the catheter surface, forming proximate to a lumen hole in said surface a balloon layer, said balloon layer being physically contiguous with said surface and without external irregularities or shoulders formed at a periphery of said balloon layer; and further
   wherein said balloon layer will form upon inflation through said lumen hole a donut-shaped balloon circumferentially about the catheter surface.

4. A balloon catheter consisting essentially of:
   a tube;
   a lumen hole in and defined by said tube;
   a balloon layer of identical material to said tube positioned circumferentially around said tube and covering said lumen hole, wherein such balloon layer
   (i) is physically contiguous with the surface of said tube, exhibiting no external irregularities or shoulders at a periphery of said balloon layer, and
   (ii) forms upon inflation through said lumen hole a donut-shaped balloon.

5. The balloon catheter according to claim 4 wherein said balloon layer returns to substantially original shape on deflation following inflation.

6. A balloon catheter comprising:
   a tube;
   a lumen hole in and defined by said tube;
   a balloon layer postioned circumferentially around said tube and covering said lumen hole, wherein said balloon layer,
   (i) is physically contiguous with the surface of said tube, exhibiting no external irregularities or shoulders at a periphery of said balloon layer, and
   (ii) forms upon inflation through said lumen hole a donut-shaped ballon;
   wherein there is neither coating material nor tape nor any solid material whatsoever between said tube and said balloon layer and within said balloon.

7. An intermediate product form of a balloon catheter comprising:
   a tube;
   a lumen hole in and defined by said tube;
   a balloon layer positioned circumferentially around said tube and covering said lumen hole, wherein said balloon layer
   (i) is physically contiguous with the surface of said tube, exhibiting no external irregularities or shoulders at a periphery of said balloon layer,
   (ii) forms upon inflation through said lumen hole a donut-shaped balloon; and
   a dissolvable layer of parting agent between said tube and said balloon layer and with said balloon, the parting agent being present within an intermediate product of the balloon catheter and being dissolved and removed in a final product balloon catheter.

8. The intermediate product form of a balloon catheter of claim 7 wherein said dissolvable layer is also mechanically fracturable.

9. The intermediate product form of a balloon catheter of claim 7 wherein said dissolvable layer is dissolvable in water.

* * * * *